United States Patent
Segawa et al.

(10) Patent No.: US 8,747,836 B2
(45) Date of Patent: Jun. 10, 2014

(54) AGENT FOR PREVENTION OF ALCOHOLIC HEPATOPATHY

(75) Inventors: Syuichi Segawa, Shibuya-ku (JP); Yoshihisa Wakita, Shibuya-ku (JP)

(73) Assignee: Sapporo Breweries Limited, Tokyo (JP)

(*) Notice: Subject to any disclaimer, the term of this patent is extended or adjusted under 35 U.S.C. 154(b) by 343 days.

(21) Appl. No.: 12/811,945

(22) PCT Filed: Jan. 14, 2009

(86) PCT No.: PCT/JP2009/050392
§ 371 (c)(1),
(2), (4) Date: Jul. 7, 2010

(87) PCT Pub. No.: WO2009/090961
PCT Pub. Date: Jul. 23, 2009

(65) Prior Publication Data
US 2010/0291051 A1    Nov. 18, 2010

(30) Foreign Application Priority Data
Jan. 15, 2008  (JP) .................................. 2008-006147

(51) Int. Cl.
*A61P 1/16* (2006.01)
*A61K 35/74* (2006.01)
*C12N 1/20* (2006.01)
*C12P 1/00* (2006.01)
*C12P 1/02* (2006.01)
*A23L 1/30* (2006.01)

(52) U.S. Cl.
CPC ... *C12P 1/00* (2013.01); *C12P 1/02* (2013.01); *A23L 1/3014* (2013.01); *A61K 35/747* (2013.01)
USPC ..................... 424/93.45; 424/115; 424/195.5; 435/252.9; 435/243; 435/317.1

(58) Field of Classification Search
USPC ...................................................... 424/93.45
See application file for complete search history.

(56) References Cited

U.S. PATENT DOCUMENTS

| | | | |
|---|---|---|---|
| 7,223,591 B2 * | 5/2007 | De Simone | 435/253.4 |
| 7,544,356 B2 * | 6/2009 | Lim et al. | 424/93.45 |
| 2007/0172549 A1 | 7/2007 | Okamoto et al. | |
| 2011/0002901 A1 | 1/2011 | Segawa et al. | |

FOREIGN PATENT DOCUMENTS

| | | |
|---|---|---|
| CN | 1853508 A | 11/2006 |
| EP | 1 652 913 A1 | 5/2006 |
| EP | 1 820 406 A1 | 8/2007 |
| EP | 2 062 968 A1 | 5/2009 |
| JP | 9-301877 | 11/1997 |
| JP | 2004 210687 | 7/2004 |
| JP | 2006 298917 | 11/2006 |
| KR | 10 2005 0042860 | 5/2005 |
| WO | WO 03013558 A1 * | 2/2003 |
| WO | 2008/023663 | 2/2008 |

OTHER PUBLICATIONS

Segawa, Shuichi et al., "Oral administration of heat-killed *Lactobacillus brevis* SBC8803 ameliorates alcoholic liver disease in ethanol-containing diet-fed C57BL/6N mice", International Journal of Food Microbiology, vol. 128, No. 2, pp. 371-377, (2008).

Segawa, Shuichi et al., "*Lactobdcillus brevis* SBC8803 Kabu no keiko Toyo ni yoru Alcohol-sei Kan Shogdi no Yokusei", Nippon Nogei Kagakukai Taikai Koen Yoshishu, vol. 2008, p. 130, (Mar. 5, 2008), (with English translation).

U.S. Appl. No. 12/438,411, filed Feb. 23, 2009, Segawa, et al.

Chinese Office Action issued Jul. 14, 2011, in Patent Application No. 200980102494.1.

Shuichi Segawa, et al. "Effect of oral administration of heat-killed *Lactobacillus brevis* SBC8803 on total and ovalbumin-specific immunoglobulin E production through the improvement of Th1/Th2 balance", International Journal of Food Microbiology, vol. 121, 2008, pp. 1-10.

Office Action as received in counterpart Japanese Application No. P2009-550020 dated Sep. 11, 2012.w/partial translation.

Shuichi Segawa, et al. "2B03p16, Investigation of antiallergic action by oral administration of *Lactobacillus brevis* SBC8803," Nippon Nogei Kagakukai Taikai Koen Yoshishu, vol. 2007, Mar. 5, 2007, p. 119 w/English Translation.

* cited by examiner

*Primary Examiner* — Blaine Lankford
*Assistant Examiner* — David Berke-Schlessel
(74) *Attorney, Agent, or Firm* — Oblon, Spivak, McClelland, Maier & Neustadt, L.L.P.

(57) ABSTRACT

The present invention provides an agent for inhibition of alcoholic hepatopathy comprising cells of a strain belonging to *Lactobacillus brevis*, or treated product thereof as an active ingredient. The agent for inhibition of alcoholic hepatopathy of the present invention is safe for living body and can be used as a component in foods and beverages.

6 Claims, 7 Drawing Sheets

AGENT FOR PREVENTION OF ALCOHOLIC HEPATOPATHY

CROSS-REFERENCE TO RELATED APPLICATIONS

This application is a National Stage of PCT/JP09/050,392 filed Jan. 14, 2009 and claims the benefit of JP 2008-006147 filed Jan. 15, 2008.

TECHNICAL FIELD

The present invention relates to an agent for inhibition of alcoholic hepatopathy.

BACKGROUND ART

With rising consumption of alcoholic beverages in recent years, demand has been increasing for an agent for inhibition of alcoholic hepatopathy.

Several agents for inhibition of alcoholic hepatopathy are known. For example, compositions obtained by certain treatment of barley spirits distillation residue have been reported to have inhibitory action against alcoholic hepatopathy (see Patent document 1).

[Patent document 1] Japanese Unexamined Patent Publication No. 2004-210687

DISCLOSURE OF THE INVENTION

Problems to be Solved by the Invention

An agent for inhibition of alcoholic hepatopathy should be safe for living body and suitable for use as a component in foods and beverages. However, such agents for inhibition of alcoholic hepatopathy have been few in type and have hitherto failed to satisfy consumer demand.

It is an object of the present invention to provide a novel agent for inhibition of alcoholic hepatopathy that is safe for living body and suitable for use as a component in foods and beverages.

Means for Solving the Problems

The present invention provides an agent for inhibition of alcoholic hepatopathy comprising cells of a strain belonging to *Lactobacillus brevis*, or treated product thereof as an active ingredient.

The agent for inhibition of alcoholic hepatopathy of the present invention can inhibit alcoholic hepatopathy, i.e. hepatopathy (fatty liver, hepatitis, hepatic fibrosis, hepatic cirrhosis, carcinoma of liver, etc.) caused by ingestion of alcoholic beverages.

*Lactobacillus brevis* has long been known as a lactic acid bacterium used in fermented foods, and its safety in living body has been established. Thus, the agent for inhibition of alcoholic hepatopathy of the present invention is highly safe for living body and can be used not only as a medicinal component but also as a component in, for example, food and beverage additives and foods and beverages.

In addition, the agent for inhibition of alcoholic hepatopathy of the present invention can be used as a component in alcoholic beverages to produce alcoholic beverages with reduced hepatopathic effects. In particular, if an agent for inhibition of alcoholic hepatopathy containing live proliferating cells is used in an alcoholic beverage, it is possible to obtain an alcoholic beverage with even further reduced hepatopathic effects.

*Lactobacillus brevis* includes the 4 subspecies *brevis, gravesensis, otakiensis* and *coagulans*. The strain in the agent for inhibition of alcoholic hepatopathy of the present invention is preferably a strain belonging to the subspecies brevis, and among strains belonging to the subspecies *brevis*, it is most preferably *Lactobacillus brevis* SBC8803. Strain SBC8803 can grow even in the presence of alcohol, and it is especially preferred for use as a component in alcoholic beverages. *Lactobacillus brevis* SBC8803 was deposited at the International Patent Organism Depositary (IPOD) of the National Institute of Advanced Industrial Science and Technology (Central 6, 1-1, Higashi 1-chome, Tsukuba City, Ibaraki Prefecture, Japan 305-8566) on Jun. 28, 2006, as FERM BP-10632.

Since the agent for inhibition of alcoholic hepatopathy of the present invention can be used as a component in medicines, food and beverage additives and foods and beverages, the present invention also provides medicines, food and beverage additives and foods and beverages comprising the agent for inhibition of alcoholic hepatopathy of the present invention.

Effect of the Invention

According to the present invention there is provided a novel agent for inhibition of alcoholic hepatopathy that is safe for living body and can be used as a component in foods and beverages. There are also provided medicines, food and beverage additives and foods and beverages comprising the agent for inhibition of alcoholic hepatopathy.

BEST MODE FOR CARRYING OUT THE INVENTION

Figure 1:
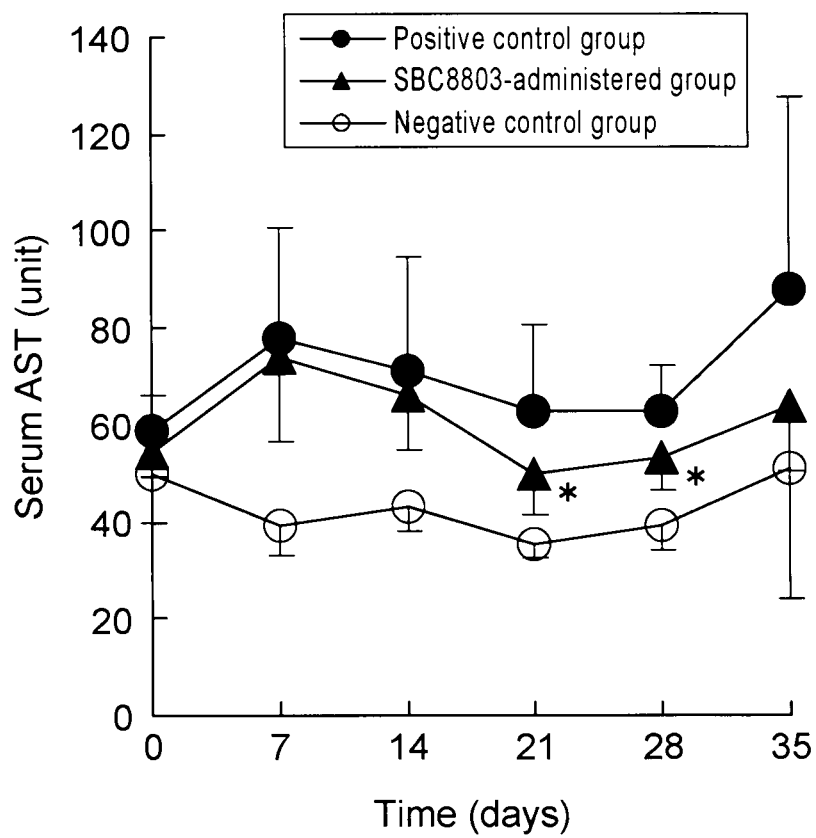
FIG. 1 is a graph showing time course of serum AST concentration in mice administered cells of *Lactobacillus brevis* SBC8803.

Preferred modes of the present invention will now be explained.

The agent for inhibition of alcoholic hepatopathy according to the present invention comprises cells of a strain belonging to *Lactobacillus brevis*, or treated product thereof as an active ingredient.

*Lactobacillus brevis* is classified into 4 subspecies [*brevis, gravesensis, otakiensis, coagulans*] based on differences in the nucleotide sequence of the 16S ribosomal DNA, and in the percentage of acid production from consumed sugars.

Strains belonging to subspecies brevis are preferred as strains belonging to *Lactobacillus brevis*, and *Lactobacillus brevis* SBC8803, for example, is preferred among strains belonging to subspecies *brevis*. *Lactobacillus brevis* SBC8803 was deposited at the International Patent Organism Depositary (IPOD) of the National Institute of Advanced Industrial Science and Technology (Central 6, 1-1, Higashi 1-chome, Tsukuba City, Ibaraki Prefecture, Japan 305-8566) on Jun. 28, 2006, as FERM BP-10632.

So long as it belongs to *Lactobacillus brevis*, the strain in the agent for inhibition of alcoholic hepatopathy of the present invention may be one that is separable from the natural environment or one that is commercially obtainable from a cell bank such as ATCC, for example.

The cells of the strain may consist of cells of only a single strain, or they may include cells of two or more different strains. The cells may be either live or dead cells. The cells can be produced in large quantity by culturing live cells. The culture medium used may be one containing a nitrogen source and a carbon source. As nitrogen sources there may be used meat extract, peptone, gluten, casein, yeast extract, amino acids and the like, and as carbon sources there may be used glucose, xylose, fructose, inositol, maltose, starch syrup, koji juice, starch, bagasse, bran, molasses, glycerin and the like. As inorganic substances, there may be added ammonium sulfate, potassium phosphate, magnesium chloride, salt, iron, manganese, molybdenum and the like, and vitamins and the like may also be added. The culturing temperature is about 25-40° C. and preferably about 27-35° C., the culturing time is about 12-48 hours, and aeration shaking may be performed. The culture medium pH is about 3-6 and preferably about 4-6.

As examples of treated product of cells there may be mentioned treated products obtained by heating cells for at least several minutes at 100° C. or higher (for example, treated products obtained by autoclave treatment of cells for 10 minutes or longer at a temperature of 110-125° C.), treated products obtained by freeze-drying and spray-drying of cells, or treated products obtained by physical disruption of cells by ultrasonic waves, French pressing or the like.

The agent for inhibition of alcoholic hepatopathy of the present invention may be in the form of a solid (for example, powder obtained by freeze-drying), liquid (water-soluble or fat-soluble solution or suspension), paste or the like, and its dosage form may be as a powder, granules, tablet, syrup, lozenge, capsules, or the like. The agent for inhibition of alcoholic hepatopathy of the present invention may be one comprising cells of a strain belonging to *Lactobacillus brevis*, or a treated product thereof.

Each of the aforementioned formulations may be prepared by mixing the cells of a strain belonging to *Lactobacillus brevis*, or its treated product, with pharmaceutically acceptable additives (an excipient, binder, lubricant, disintegrator, emulsifier, surfactant, base, dissolving aid, suspending agent or the like).

As examples of excipients there may be mentioned lactose, sucrose, starch and dextrin, for example. As binders there may be mentioned polyvinyl alcohol, gum arabic, tragacanth, gelatin, hydroxypropylmethylcellulose, hydroxypropylcellulose, carboxymethylcellulose sodium and polyvinylpyrrolidone, for example. As lubricants there may be mentioned magnesium stearate, calcium stearate and talc, for example. As examples of disintegrators there may be mentioned crystalline cellulose, agar, gelatin, calcium carbonate, sodium hydrogencarbonate and dextrin. As emulsifiers or surfactants there may be mentioned Tween60, Tween80, Span80 and glycerin monostearate, for example. As bases there may be mentioned cetostearyl alcohol, lanolin, polyethylene glycol, rice bran oil, fish oil (DHA, EPA and the like) and olive oil, for example. As dissolving aids there may be mentioned polyethylene glycol, propylene glycol, sodium carbonate, sodium citrate and Tween80, for example. As suspending agents there may be mentioned the aforementioned surfactants, as well as polyvinyl alcohol, polyvinylpyrrolidone, methylcellulose, hydroxymethylcellulose and sodium alginate, for example.

The agent for inhibition of alcoholic hepatopathy of the present invention can be used as a component in medicines, food and beverage additives, and foods and beverages.

For example, the agent for inhibition of alcoholic hepatopathy of the present invention may be used as an additive in foods and beverages such as water, soft drinks, fruit drinks, milk beverages, alcoholic beverages, bread, noodles, rice products, tofu, dairy products, soy sauce, miso, confectioneries and the like. These foods and beverages may contain other additives commonly used in the field, and examples of such additives include bittering agents, aromas, apple fiber, soybean fiber, meat extract, black vinegar extract, gelatin, corn starch, honey, animal or vegetable fats and oils, monosaccharides such as glucose and fructose, disaccharides such as sucrose, polysaccharides such as dextrose and starch, sugar alcohols such as erythritol, xylitol, sorbitol and mannitol, and vitamins such as vitamin C. The agent for inhibition of alcoholic hepatopathy according to the present invention may also be used as a component in specified health foods, special use foods, nutritional supplements, health foods, functional foods, patient foods and the like. Foods and beverages containing the agent for inhibition of alcoholic hepatopathy of the present invention may be fermentates obtained by fermentation of milk, nonfat milk, soybean milk, or the like with strains belonging to *Lactobacillus brevis*.

The agent for inhibition of alcoholic hepatopathy of the present invention may be administered to a human or to a non-human mammal. The administration dosage and method of administration may be appropriately determined according to the condition and age of the individual to which it is administered. Oral administration may be mentioned as an example of a suitable administration method.

According to the present invention, "agent for inhibition of alcoholic hepatopathy" means an agent that inhibits alcoholic hepatopathy, i.e. hepatopathy (fatty liver, hepatitis, hepatic fibrosis, hepatic cirrhosis, carcinoma of liver, etc.) caused by ingestion of alcoholic beverages. The term "hepatopathy" may be undeveloped hepatopathy with future onset or already existing hepatopathy, and "inhibit" includes prevention, cure, reduction, alleviation, and the like. Inhibition of hepatopathy can be judged, for example, by inhibition of increase in serum AST (aspartate amino transferase) or serum ALT (alanine amino transferase), or accumulation of fat (cholesterol, triglycerides, etc.) in the liver, that accompanies ingestion of alcohol.

EXAMPLES

The present invention will now be explained in greater detail based on test examples. However, the present invention is not limited to the test examples described below.

In the following test examples there were used 7-week-old male C57BL/6N mice (Charles River Laboratories, Japan Inc.), raised in an SPF environment under conditions with a temperature of 23±1° C., a humidity of 55±10%, and a light/dark cycle of 12 hours (light period: 8:00-20:00, dark period:

20:00-8:00). The animals were handled according to the "Guidelines for Proper Conduct of Animal Experiments" (Science Council of Japan).

The following test examples were carried out with the mice divided into 3 groups. Each group of the mice were given the specified feed or bacterial strain for 35 days (Test Example 1) or 49 days (Test Examples 2-4).
Positive control group: Group given ethanol-added feed (8 individuals) SBC8803-administered group: Group given ethanol-added feed and *Lactobacillus brevis* SBC8803 strain (8 individuals)
Negative control group: Group given control feed (ethanol-free feed) (7 individuals)

The compositions of the ethanol-added feed and the control feed were as shown in Table 1. In Table 1, the component amounts are listed as grams (g) per 1 L of feed.

TABLE 1

|  | Ethanol-added feed | Control feed |
| --- | --- | --- |
| Casein sodium | 41.4 | 41.4 |
| l-cysteine | 0.5 | 0.5 |
| dl-methionine | 0.3 | 0.3 |
| Corn oil | 8.5 | 8.5 |
| Olive oil | 28.4 | 28.4 |
| Safflower oil | 2.7 | 2.7 |
| Vitamins | 2.5 | 2.5 |
| Minerals | 8.75 | 8.75 |
| Maltose-dextrin equivalent mixture | 25.6 | 115.2 |
| Cellulose | 10 | 10 |
| Choline bitartrate | 0.53 | 0.53 |
| Xanthan gum | 3 | 3 |
| Ethanol | 50 | 0 |
| Total | 182.18 | 221.78 |

[Preparation of Test Samples]

Cells of *Lactobacillus brevis* SBC8803 were sterilized by autoclave treatment (121° C., 20 min) and then freeze-dried, and the freeze-dried cells were suspended in distilled water to obtain 100 mg/mL of a cell suspension. In the following test examples, administration of strain SBC8803 to the SBC8803-administered group was carried out by oral administration of 100 μL cell suspension/mouse/day (10 mg cells/mouse/day), using a feeding tube. *Lactobacillus brevis* SBC8803 was deposited at the International Patent Organism Depositary (IPOD) of the National Institute of Advanced Industrial Science and Technology (Central 6, 1-1, Higashi 1-chome, Tsukuba City, Ibaraki Prefecture, Japan 305-8566) on Jun. 28, 2006, as FERM BP-10632.

Test Example 1

Measurement of Serum Ast and Serum ALT

The mice in the positive control group, SBC8803-administered group and negative control group were given the prescribed feed or strain for 35 days. The serum AST (aspartate amino transferase) concentrations (unit) and serum ALT (alanine amino transferase) concentrations (unit) of the mice were measured on the 7th, 14th, 21st, 28th and 35th days. Measurement of the serum AST and serum ALT concentrations was conducted using a Wako Transaminase CII-Test Kit (Wako Pure Chemical Industries, Ltd.). Serum AST and serum ALT concentrations can be used as markers of hepatopathy.

Figure 2:
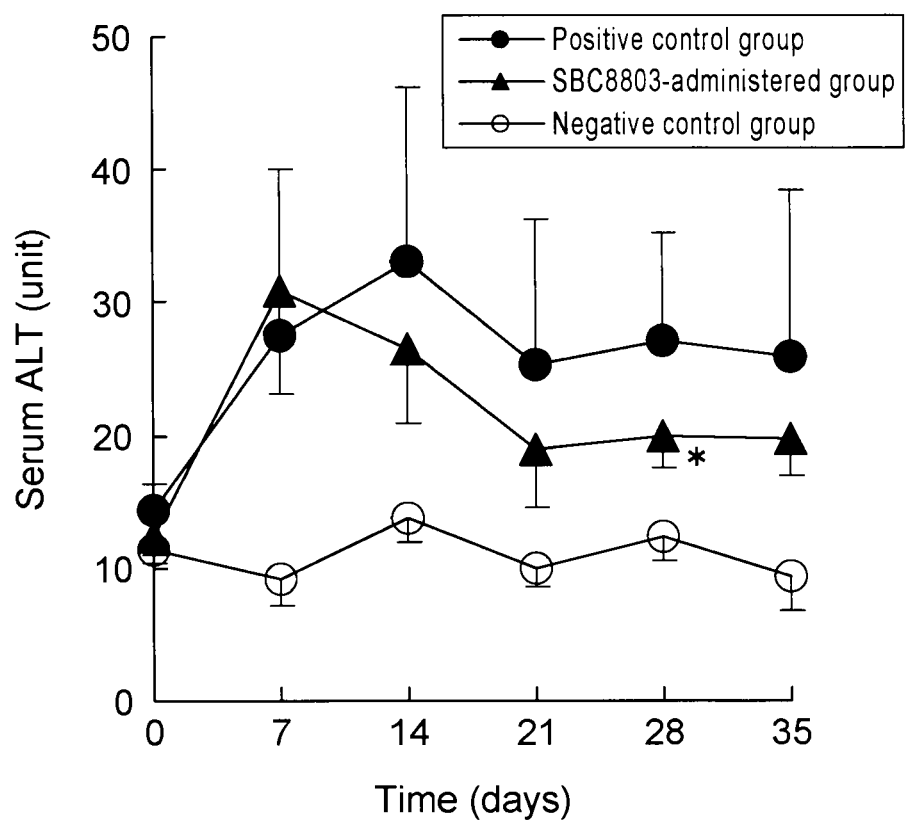
FIG. 2 is a graph showing time course of serum ALT concentration in mice administered cells of *Lactobacillus brevis* SBC8803.

The results are shown in FIG. 1 and FIG. 2. FIG. 1 is a graph showing the time course of serum AST concentration in the mice of each group. FIG. 2 is a graph showing the time course of serum ALT concentration in the mice of each group. The data shown in FIGS. 1 and 2 are represented as mean±SD. The "*" symbols attached to the data indicate that the data showed a significant difference (significance level: 5%) compared to the positive control group. Significant difference was judged using the Student t-test.

As clearly seen by the results of Test Example 1 (FIGS. 1 and 2), after the 7th day, the serum AST and serum ALT concentrations were markedly higher values in the positive control group compared to the negative control group. In the SBC8803-administered group, however, after the 21st day, the serum AST and serum ALT concentrations were significantly lower values compared to the positive control group.

Test Example 2

Measurement of Total Cholesterol and Triglyceride Content in the Liver

The mice in the positive control group, SBC8803-administered group and negative control group were given the prescribed feed or strain for 49 days. On the 49th day, the total cholesterol and triglyceride content in the liver in the mice were measured. Measurement of the total cholesterol and triglyceride content in the liver was carried out using a Wako Cholesterol E-Test Kit (Wako Pure Chemical Industries, Ltd.) and a Wako Triglyceride E-Test Kit (Wako Pure Chemical Industries, Ltd.). The total cholesterol and triglyceride content in the liver can be used as markers of hepatopathy (especially fatty liver).

Specifically, the mice were starved from the previous day, and on the 49th day, blood was sampled from the inferior vena cava of the mice and then the livers were excised and the liver weights measured. The livers were placed in 0.25% sucrose solution containing 1 mM EDTA and homogenized for 10 seconds with a microhomogenizer. After adding 3 mL of chloroform/methanol (2:1 v/v) to 3 mL of the liver homogenate, it was mixed for 1 minute with a vortex mixer and the liver lipids were extracted. After centrifugation (3000 rpm, 10 min), the chloroform/methanol layer was collected and 0.5 mL thereof was dried with a concentrating centrifuge. To the extracted lipids there was added 0.5 mL of an aqueous solution of 1% fatty acid-free bovine serum albumin (BSA) to prepare a suspension, and the total cholesterol (mg/g liver) and triglyceride (mg/g liver) content were measured using the kit described above. The total cholesterol and triglyceride amounts per unit liver weight (wet) were calculated from the weights of the excised livers.

Figure 3:
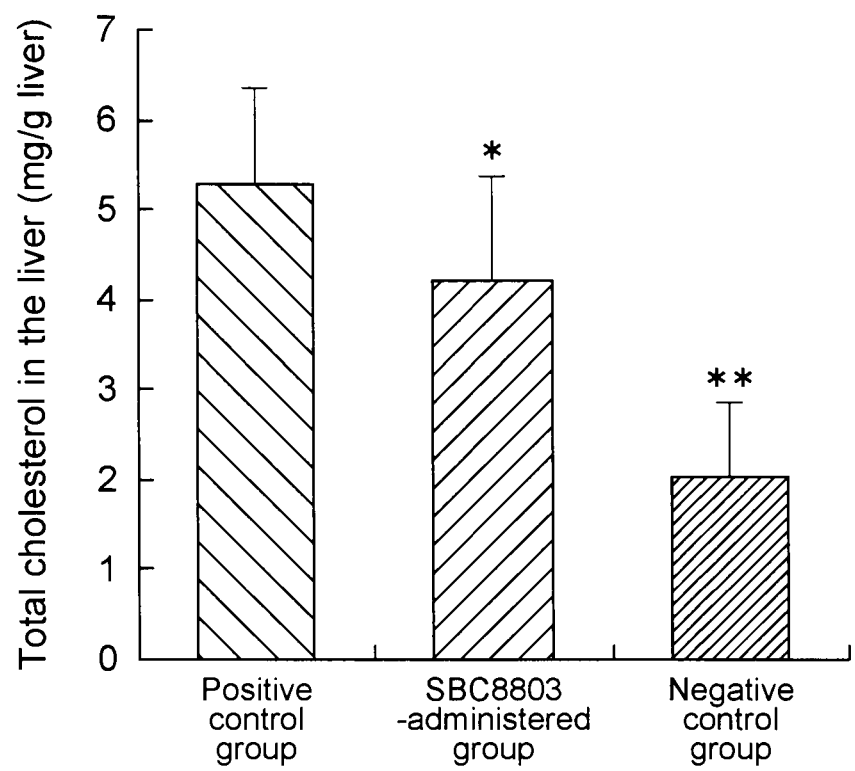
FIG. 3 is a graph showing total cholesterol content in the liver of mice administered cells of *Lactobacillus brevis* SBC8803.
Figure 4:
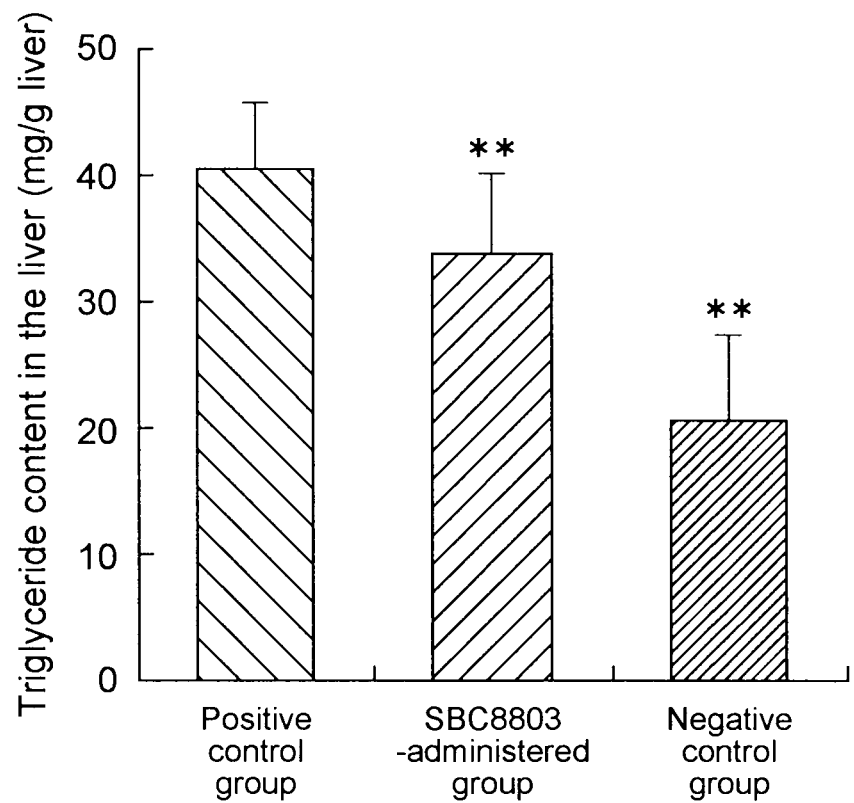
FIG. 4 is a graph showing triglyceride content in the liver of mice administered cells of *Lactobacillus brevis* SBC8803.

The results are shown in FIG. 3 and FIG. 4. FIG. 3 is a graph showing total cholesterol content in the livers of the mice of each group. FIG. 4 is a graph showing the triglyceride content in the liver of the mice in each group. The data shown in FIGS. 3 and 4 are represented as mean±SD. The "*" and "**" symbols attached to the data indicate that the data showed a significant difference (significance levels: 5% and 1%, respectively) compared to the positive control group. Significant difference was judged using the Student t-test.

As clearly seen by the results for Test Example 2 (FIGS. 3 and 4), the total cholesterol and triglyceride content in the liver were markedly higher values in the positive control group compared to the negative control group. In the SBC8803-administered group, however, the total cholesterol and triglyceride content in the liver were significantly lower values compared to the positive control group.

Test Example 3

Preparation of Liver Histologic Specimens

Portions of the livers excised in Test Example 2, for 3 individuals of the positive control group, 3 individuals of the SBC8803-administered group and 2 individuals of the negative control group, randomly selected, were fixed with 10% formalin solution, and histologic samples (Oil Red O stain) were prepared.

The Oil Red O stains of the mice livers of the positive control group were fully tinged red and large macrovesicular steatosis was also observed. The presence of macrovesicular steatosis was also confirmed in the SBC8803-administered group, but the number was smaller than in the positive control group. Inhibition of alcoholic fatty liver onset by administration of *Lactobacillus brevis* SBC8803 was also confirmed based on Oil Red O staining.

Test Example 4

Measurement of TNF-α, SREBP-1 and SREBP-2 Expression Level in Liver

The mice in the positive control group, SBC8803-administered group and negative control group were given the prescribed feed or strain for 49 days. On the 49th day, the mouse livers were excised and the total RNA was extracted using Trizol (Invitrogen Corp.) and purified with an RNeasy Mini Kit (Qiagen Inc.). Also, cDNA was prepared from the RNA using a QuantiTect Reverse Transcription Kit (Qiagen Inc.), and real time PCR was performed with SYBR Green to measure the TNF-α mRNA, SREBP-1 mRNA and SREBP-2 mRNA levels. TNF (Tumor Necrosis Factor)-α is a cytokine that promotes the inflammatory response, and SREBP (Sterol Regulatory Element-Binding Protein)-1 and -2 are transcription factors that promote de novo synthesis of triglycerides and cholesterol.

Figure 5:
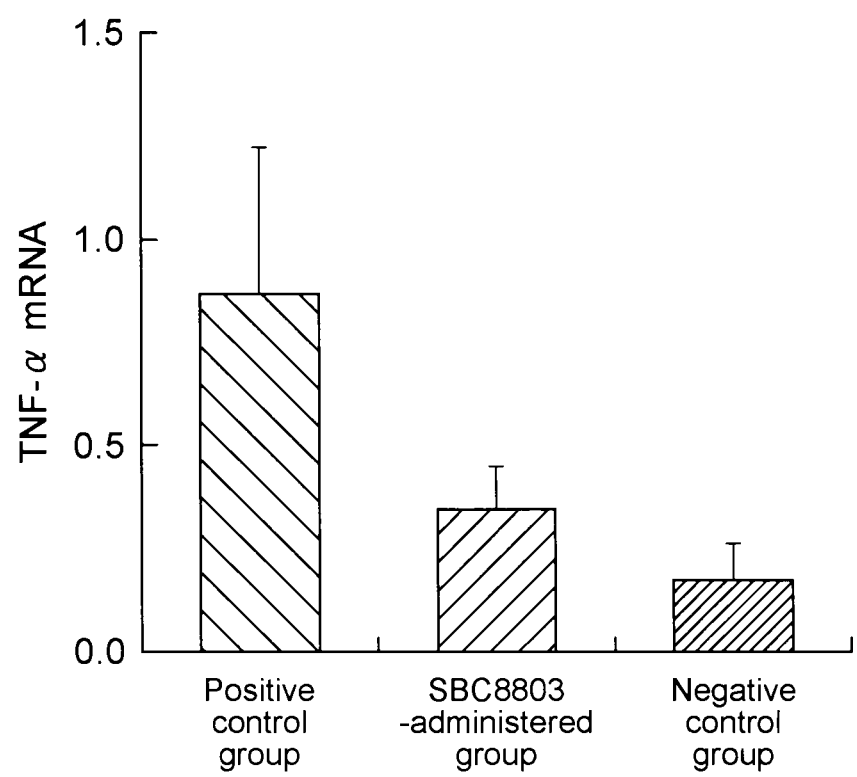
FIG. 5 is a graph showing TNF-α, mRNA levels in the liver of mice administered cells of *Lactobacillus brevis* SBC8803.
Figure 6:
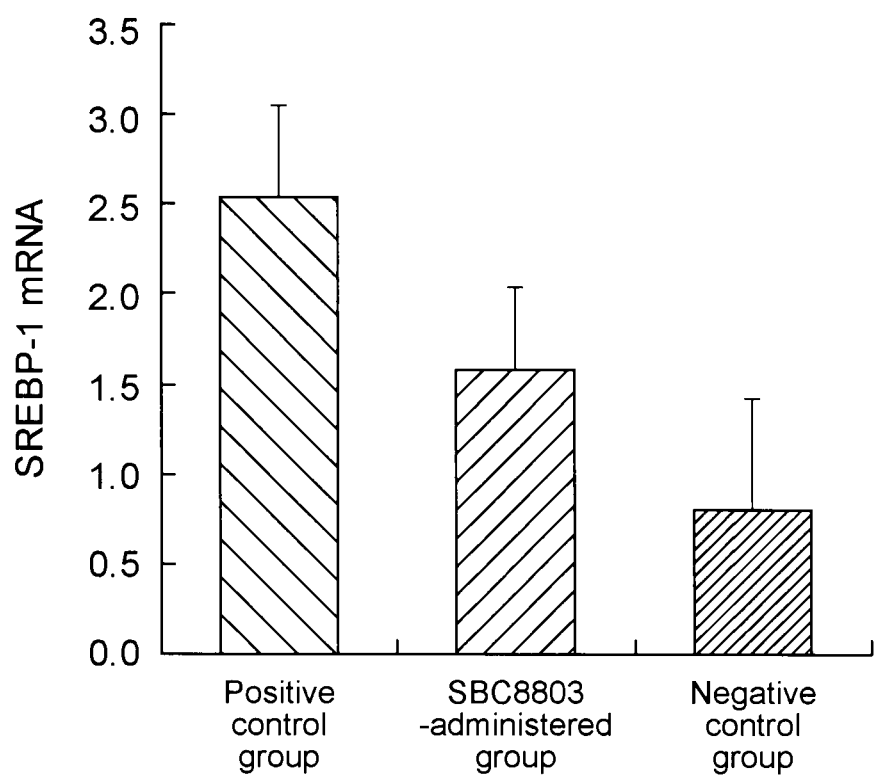
FIG. 6 is a graph showing SREBP-1 mRNA levels in the liver of mice administered cells of *Lactobacillus brevis* SBC8803.
Figure 7:
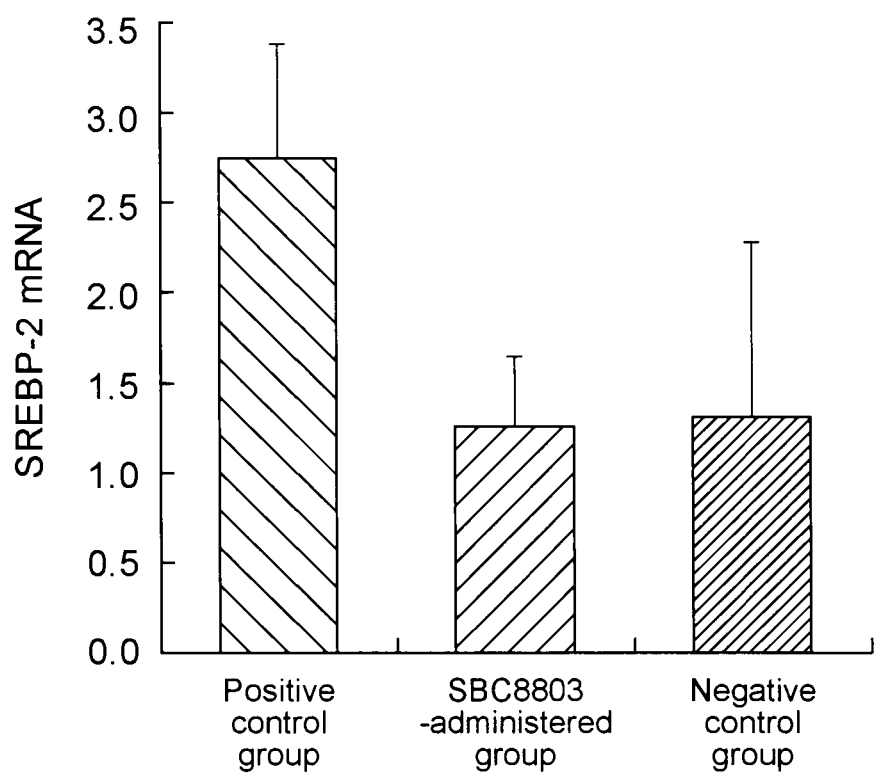
FIG. 7 is a graph showing SREBP-2 mRNA levels in the liver of mice administered cells of *Lactobacillus brevis* SBC8803.

The results are shown in Table 2 and FIGS. 5 to 7. FIG. 5 is a graph showing TNF-α mRNA levels in the livers of the mice of each group. FIG. 6 is a graph showing SREBP-1 mRNA levels in the livers of the mice of each group. FIG. 7 is a graph showing SREBP-2 mRNA levels in the livers of the mice of each group. In Table 2 and FIGS. 5 to 7, the TNF-α mRNA, SREBP-1 mRNA and SREBP-2 mRNA levels are shown as ratios with respect to simultaneously measured GAPDH (glyceraldehyde-3-phosphate dehydrogenase) mRNA (mean±SD).

TABLE 2

|  | TNF-α | SREBP-1 | SREBP-2 |
|---|---|---|---|
| Positive control group | 0.868 ± 0.353 | 2.543 ± 0.503 | 2.744 ± 0.643 |
| SBC8803-administered group | 0.346 ± 0.103 | 1.577 ± 0.459 | 1.252 ± 0.397 |
| Negative control group | 0.170 ± 0.091 | 0.801 ± 0.624 | 1.313 ± 0.972 |

As seen by the results of Test Example 4 (Table 2, FIGS. 5 to 7), expression level of TNF-α, SREBP-1 and SREBP-2 in the livers was markedly higher in the positive control group than in the negative control group. In the SBC8803-administered group, however, expression level of TNF-α, SREBP-1 and SREBP-2 in the livers was markedly lower compared to the positive control group.

These test examples confirmed that using an agent for inhibition of alcoholic hepatopathy of the present invention can inhibit hepatopathy caused by ingestion of alcoholic beverages.

INDUSTRIAL APPLICABILITY

The agent for inhibition of alcoholic hepatopathy of the present invention can be used for prevention or treatment of alcoholic hepatopathy.

The invention claimed is:

1. A method of inhibiting alcoholic hepatopathy in a subject in need thereof, the method comprising administering to the subject a treated product of *Lactobacillus brevis* SBC8803 (FERM BP-10632) as an active ingredient;
   wherein the treated product is obtained by autoclaving the cells for at least 10 minutes at 100° C. or more.

2. The method according to claim 1, wherein the at least one cell is administered in a medicinal product.

3. The method according to claim 1, wherein the at least one cell is administered in food or beverage.

4. A method of treating alcoholic hepatopathy in a subject in need thereof, the method comprising administering to the subject a treated product of *Lactobacillus brevis* SBC8803 (FERM BP-10632) as an active ingredient;
   wherein the treated product is obtained by autoclaving the cells for at least 10 minutes at 100° C. or more.

5. The method according to claim 4, wherein the at least one cell is administered in a medicinal product.

6. The method according to claim 4, wherein the at least one cell is administered in food or beverage.

* * * * *